United States Patent [19]

Peñáz

[11] Patent Number: 4,869,261

[45] Date of Patent: Sep. 26, 1989

[54] AUTOMATIC NONINVASIVE BLOOD PRESSURE MONITOR

[75] Inventor: Jan Peñáz, Brno, Czechoslovakia

[73] Assignee: University J.E. Purkyne v Brne, Brno, Czechoslovakia

[21] Appl. No.: 171,601

[22] Filed: Mar. 22, 1988

[30] Foreign Application Priority Data

Mar. 27, 1987 [CS] Czechoslovakia ............ 2135-87

[51] Int. Cl.⁴ .................................................. A61B 5/02
[52] U.S. Cl. ........................................ 128/667; 128/677; 128/681; 128/694
[58] Field of Search ..................... 128/664–667, 128/672, 677–686, 687, 691, 694

[56] References Cited

U.S. PATENT DOCUMENTS

| 4,030,485 | 6/1977 | Warner | 128/667 |
| 4,475,554 | 10/1984 | Hyndman | 128/667 X |
| 4,510,940 | 4/1985 | Wesseling | 128/681 X |
| 4,524,777 | 6/1985 | Kisioka et al. | 128/694 X |
| 4,539,997 | 9/1985 | Wesseling et al. | 128/681 X |

Primary Examiner—Kyle L. Howell
Assistant Examiner—Angela D. Sykes
Attorney, Agent, or Firm—Klein & Vibber

[57] ABSTRACT

An automatic noninvasive blood pressure monitor with a continuous correction of the setpoint and of the gain without interruptions of the blood pressure measurement has a pressure vibration generator, the frequency of vibration being higher than that of the highest harmonic component of blood pressure wave, and a correction circuit, the input of which is connected either directly or through at least one amplifier of the basic servosystem to the sensor of the plethysmographic gauge and output of which is fed to the input of the circuit for correction of the setpoint of the basic servosystem.

11 Claims, 3 Drawing Sheets

AUTOMATIC NONINVASIVE BLOOD PRESSURE MONITOR

BACKGROUND OF THE INVENTION (a) Field of the Invention

The invention relates to an automatic noninvasive blood pressure monitor, i.e. an instrument for measuring the blood pressure in man on arteries being compressible from the surface by means of a pressure cuff or a pelotte equipped with a plethysmographic gauge, such as an impedance or a photo-electric one, which gauge is connected through at least one amplifier and a phase corrector to an electro-pressure transducer. All these components constitute the closed loop of a servosystem which continuously and instantaneously changes the pressure in the cuff and maintains thus the volume of the artery at a value corresponding to the zero tension of the arterial wall. The pressure within the cuff thus follows the instantaneous value of intraarterial pressure. In such instruments automatic setting and correction of the setpoint and gain is also possible.

(b) Description of the Prior Art

Similar instruments are known from the patent literature, e.g. Czechoslovak patent specification No. 133205, U.S. patent specification No. 4,510,940, as well as from articles in medical and technical journals. The instruments known up to now, however, either have no automatic initial setting of the setpoint and gain, or have no correction of these parameters during the measurement. Although an instrument with such a correction has been proposed, the correction is performed during short-lasting interruption of the measurement. Another instrument proposed is equipped with an additional cuff placed on another circulatory region so that a pair of cuffs is necessary. The proposed instruments permit measurement of the blood pressure on arteries of the finger or of another region which can easily be transilluminated, however continuous blood pressure measuring is impossible on other arteries especially on larger ones.

SUMMARY OF THE INVENTION

It is therefore a primary object of the present invention to provide an automatic noninvasive blood pressure monitor with a continuous correction of the setpoint and of the gain without interruptions of the blood pressure measurement.

The basic servosystem loop is completed by a pressure vibration generator, the frequency of vibration being higher than that of the highest harmonic component of blood pressure wave, and by a correction circuit, the input of which is connected either directly or through at least one amplifier of the basic servosystem to the sensor of the plethysmographic gauge and output of which is fed to the input of the circuit for correction of the setpoint of the basic servosystem.

The instrument thus contains, in difference from similar known instruments, a generator producing pressure vibrations which are superimposed on the basic pressure wave in the cuff or the pelotte, and a correction circuit which continuously observes the oscillations of the vascular volume which are brought about by the pressure vibrations and which circuit derives a correction signal from their amplitude and/or phase during each pulse interval. The correction signal is fed, after its integration, to the basic servosystem where it adjusts its setpoint, i.e. the extent of compression of the vessel on which the measurement is being performed. In fact, the correction circuit measures, parallely with the blood pressure, the so called dynamic vascular compliance which is in a close relation to the vascular wall tension and which adjusts this tension to a value which is optimal for the transmural pressure transmission. Also, the circuit for the automatic gain control works on a similar basis, i.e. measurement of volume oscillations produced by pressure vibrations. The plethysmographic gauge of the pressure cuff or pelotte uses, in contrast to known similar instruments, the reflexion photoelectric plethysmography.

When compared with known instruments of this kind, the inventive instrument presents many advantages. The correction of the setpoint and of the gain is continuous, i.e. the blood pressure measurement runs without periodical interruptions. The correction is derived from the signal of the same gauge which provides the function of the basic servosystem and does not need therefore another gauge. The instrument is thus simpler from the standpoint both of the user and the producer. The possibility of using another gauge remains, however, as shown in the alternative embodiment of the instrument. The correction is very effective and fast so that the instrument does not need any algorithm for finding the initial setpoint. Using the reflexion photoelectric plethysmograph as a sensor for measuring the arterial volume makes it possible to measure, in a noninvasive way, the blood pressure not only in the finger but also in other arteries accessible from the surface.

BRIEF DESCRIPTION OF THE DRAWING

The foregoing and other objects, the features and the advantages of the present invention will be pointed out in, or apparent from, the following description of the preferred embodiments considered together with the accompanying drawings in which.

DESCRIPTION OF THE PREFERRED EMBODIMENTS

The basic embodiment and a preferred embodiment of the present invention will now be described with reference to the drawings.

Figure 1:
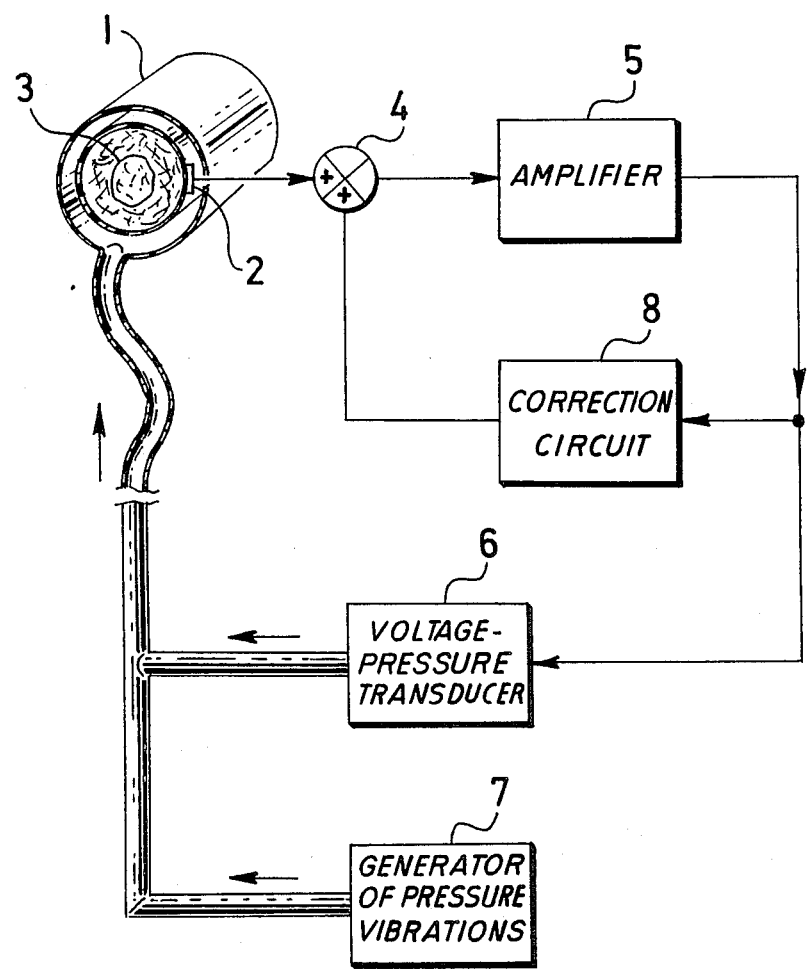
FIG. 1 is a circuit block diagram of the basic embodiment of the automatic noninvasive blood pressure monitor according to the invention.

FIG. 1 is a block diagram illustrating the construction o the basic embodiment of the present invention. In the figure, reference number 1 denotes a pressure cuff. The pressure cuff 1 is provided with a plethysmographic gauge 2 of the arterial volume and surrounds the measured zone 3. The plethysmographic gauge 2 is connected through a summing member 4 to an amplifier 5, the output of which amplifier 5 is connected to a voltage-pressure transducer 6. The pressure cuff 1 is connected fluidically on the one hand to the voltage-pressure transducer 6 on the other hand to a generator 7 of pressure vibrations. The output of the amplifier 5 is also connected to a correction circuit 8 the output of which is connected to the summing member 4.

The pressure cuff 1, the summing member 4, the amplifier 5 and the voltage-pressure transducer 6 make up the loop of the basic servosystem which servosystem keeps the artery volume of the measured zone 3 at a constant value by immediate pressure changes in the pressure cuff 1. The artery is compressed so that the vascular wall has a zero tension. Only under this condition does the pressure in the pressure cuff 1 correspond to the intraarterial pressure. Such a state is tested by means of pressure vibrations produced by the generator 7 of pressure vibrations, the correction circuit 8 producing the necessary correction signal. This correction signal is brought in the corresponding polarity to the summing member 4, adjusting continuously the compression degree of the vascular volume so that the condition of the zero tension of the vascular wall is fulfilled.

Figure 2:
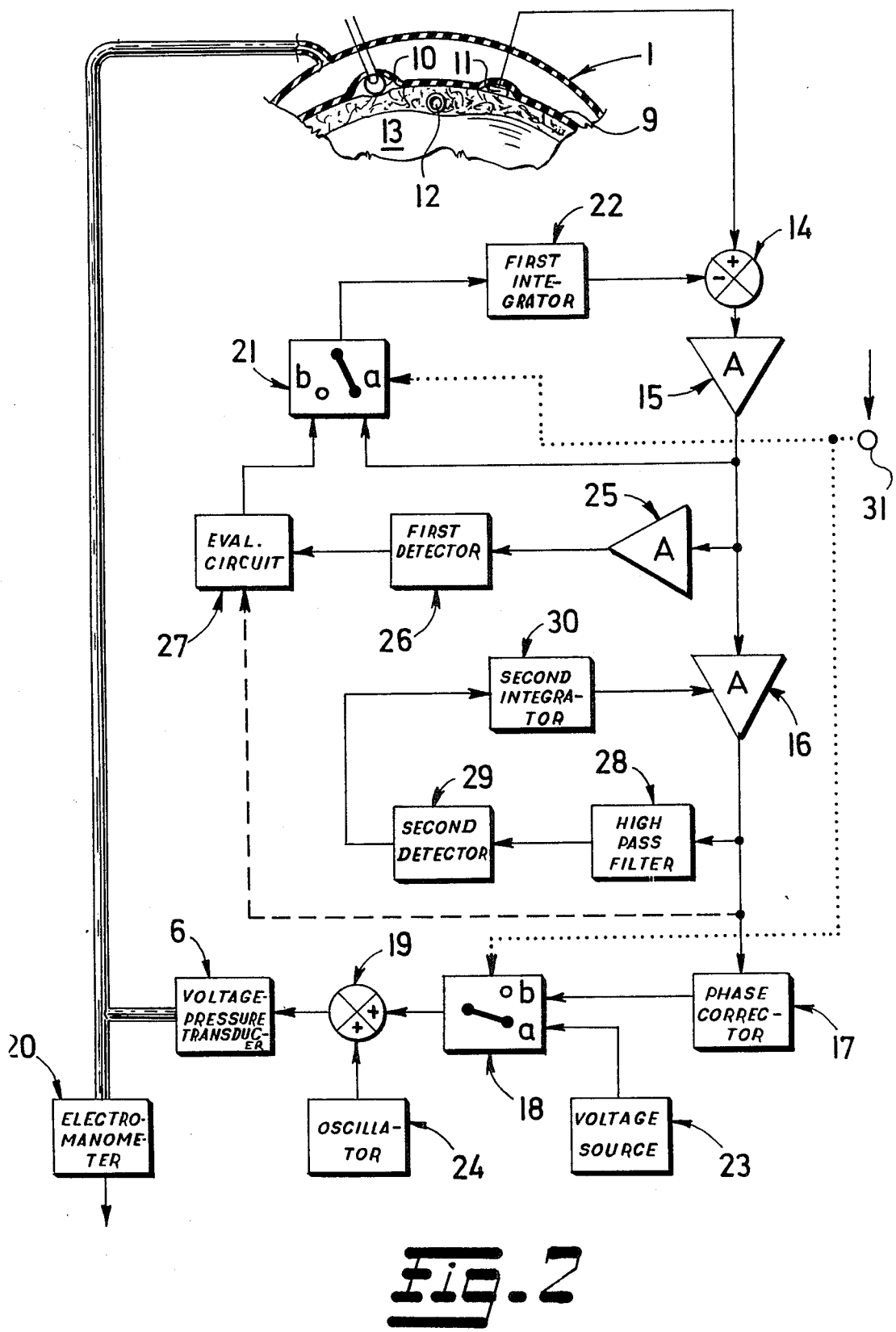
FIG. 2 is a circuit block diagram of a preferred embodiment of the automatic noninvasive blood pressure monitor according to the invention.

The preferred embodiment of the automatic noninvasive blood pressure monitor according to the invention is shown in FIG. 2. The pressure cuff 1 is applied in a suitable region, such as, e.g. finger, forearm, temporal region, etc., where the artery 12 lies in a soft tissue against a natural background e.g. the bone 13 or an artificial support. A light source 10 and a light sensor 11 are placed on the inner sheet of the pressure cuff 1 in such a manner that the artery 12 is in their neighborhood or between them.

The light sensor 11 is connected through a first summing member 14 to a first amplifier 15, the output of which is connected through a second switch 21 and a first integrator 22 with changed polarity back to the first summing member 14. The output of the first amplifier 15 is connected, in addition, to second amplifier 16 with an electronic gain control.

The second amplifier 16 is connected through a phase corrector 17 and through a first switch 18 and a second summing member 19 to the voltage-pressure transducer 6 which transducer is connected to the pressure cuff 1 and an electromanometer 20. The output of the first amplifier 15 is connected also to a narrow band amplifier 25 the output of which is connected through a first detector 26 to an evaluating circuit 27 connected to the first switch 21.

The controlling input of the evaluating circuit 27 is connected to the output of the second amplifier 16. The output signal of the second amplifier 16 is fed also through a high pass filter 28 and a second detector 29 to a second integrator 30 the output tension of which controls the gain of the second amplifier 16.

The first switch 18 and the second switch 21 are controlled by an external signal fed to a controlling input 31.

The first switch 18 is connected to a voltage source 23, the second summing member to an oscillator 24.

The function of the instrument is controlled by the first switch 18 and the second switch 21. Before starting the measurement it is necessary to put both switches 18,21 to the position a. In this position a of the switches 18,21, the loop of the basic servosystem is open, the pressure in the pressure cuff 1 corresponds to the voltage set in the voltage source 23 and the automatic zeroing loop is closed, i.e. the first integrator 22 compensates gradually the d.c. component of the photoelectric voltage of the light sensor 11 which corresponds to the volume of the artery 12. After a few seconds the output voltage of the first amplifier 15 is put to zero and the switches 18,21 are set to position b.

If the correction signal of the output of the evaluating circuit 27 is zero, then the output voltage of the first integrator 21 will not change and servosystem will keep the photoelectric signal from the light sensor 11 corresponding to the volume of the artery 12 at its original value. In this situation any change of vascular volume produces an instantaneous change of pressure in the pressure cuff 1 which compensates the volume change almost without any rest error, if the gain of the second amplifier 16 has been properly set and thanks to the phase corrector 17 which has the properties of a PID controller.

If the initial volume was chosen in a way that the arterial wall had a zero tension, then the pressure in the pressure cuff 1 and thus even the output voltage of the electromanometer 20 corresponds in each instance to the intraarterial pressure.

In practice however one can estimate the initial vascular volume, i.e. the setpoint of the servosystem only with difficulties and moreover, it is known that its value can change during the measurements. Therefore, in the instrument the required setpoint is found automatically and corrected continuously so that small pressure vibrations are superimposed on the recorded pressure course, the frequency of which exceeds any frequency naturally contained in the pressure wave. The oscillator 24 is the source of these vibrations, the output periodical voltage of which oscillator is added to the output voltage of the phase corrector 17 in the second summing member 19.

The voltage pressure transducer 6 generates then the required pressure course. The superimposed pressure vibrations in the pressure cuff 1 then produce small but measureable oscillations of the volume of the artery 12 which are recorded together with the original photoelectric signal by the light sensor 11, amplified by the first amplifier 15, then separated and further amplified by the narrow band amplifier 25 which is tuned on the frequency of the oscillator 24 and then detected by the first detector 26. The output signal of this detector 26 corresponds to the physiological variable called dynamic vascular compliance (DVC) which markedly depends on the arterial wall tension.

Figure 3:
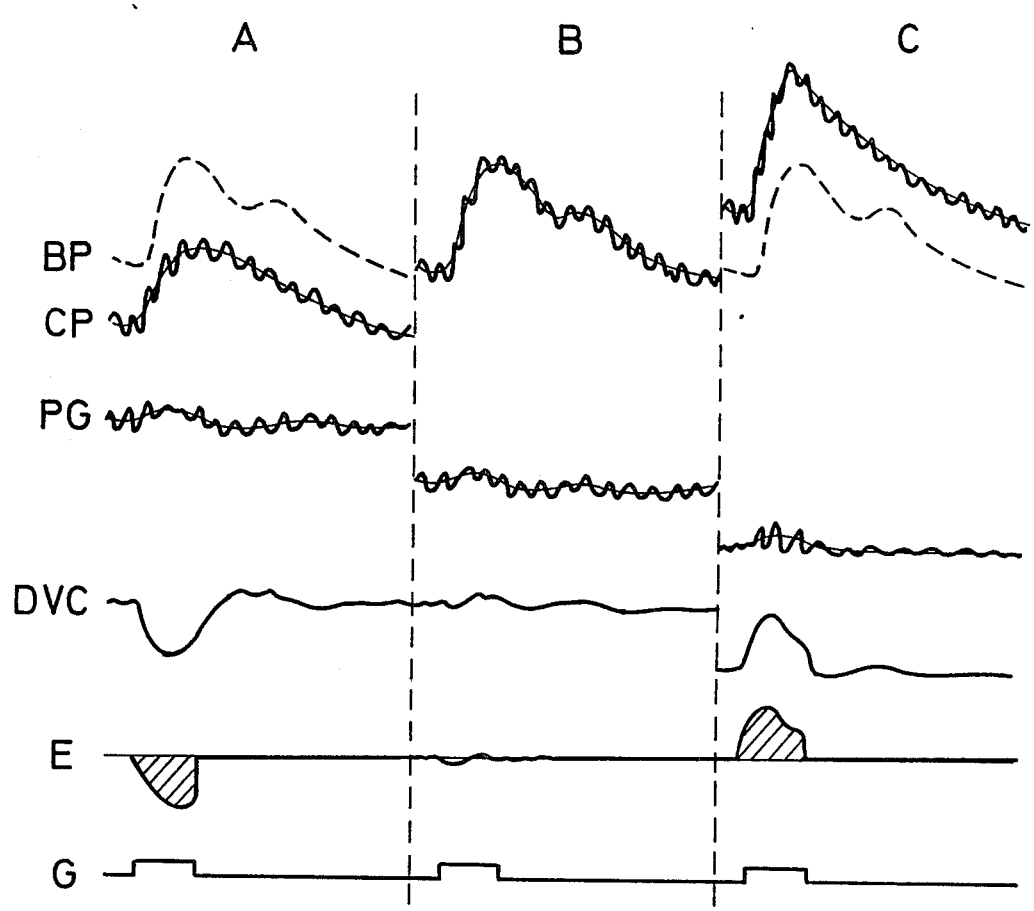
FIG. 3 shows waveforms and curves for illustrating the operation of the circuit shown in FIGS. 1 and 2.

As shown in FIG. 3, the rest error of the photoelectric signal i.e. a small increase of vascular volume PG in the systolic part of each beat is accompanied by a characteristic change of DVC in dependence on setting the servosystem setpoint. As illustrated in section A of FIG. 3, in case the setpoint is set incorrectly so that the vascular volume PG is kept by the servosystem at too high a value, then the recorded pressure CP is lower than the real intraarterial pressure BP (dashed line) and DVC decreased at the increase of vascular volume during the rest error deviation. The opposite case is illustrated in section C of FIG. 3. If the vessels are too much compressed by the servosystem which then measures an incorrectly high pressure, then DVC increases markedly at the onset of the beat. When correctly setting the pressure monitor (section B), the vascular volume PG has a medium value and the registered pressure CP is identical with the intraarterial pressure BP.

The evaluating circuit 27 (FIG. 2) of the instrument which in principle is a gated amplifier triggered by the rest error signal obtained at the output of the second amplifier 15, detects just this transient deviation of DVC at the onset of each beat, and derives from it the error signal E (see FIG. 3) and feeds it to the first integrator 22 the output voltage of which estimates the setpoint of the servosystem by means of the first summing member 14. In this way, the degree of arterial compression is automatically and continuously corrected so that the arterial wall tension is minimal.

A continual control of amplification is provided by the second amplifier 16 (FIG. 2) with electronic gain control and by the circuit comprising the high pass filter 28, the second detector 29 and the second integrator 30. From the output signal of the second amplifier 16, the high pass filter 28 selects higher frequencies than is the lowest presumed frequency of the servosystem's own oscillations and also the oscillations produced by intentionally induced pressure vibrations in the cuff. Such frequency components are a.c. amplified and detected by the second detector 29 and integrated by the second integrator 30 to which is fed also a constant voltage estimating the necessary gain of the servosystem. The output voltage of the second integrator 30 thus keeps the gain of the second amplifier 16 at a value which is safely lower than the value at which undamped oscillations of the servosystem would arise.

What is claimed is:

1. An automatic noninvasive blood pressure monitor for measuring blood pressure in arteries compressible from the surface, comprising
    a pressure means chosen from the group consisting a cuff and a pelotte, said pressure means equipped with a plethysmographic gauge of vascular volume;
    first summing means, amplifier means, a phase corrector, a first switch, and a voltage-pressure transducer;
    said guage being connected serially through said first summing means, said amplifier means, said phase corrector and said first switch to said voltage-pressure transducer, said transducer being connected to said pressure means; and
    a correction circuit having an input and an output, the input of said correction circuit being connected to said amplifier means, the output of the said correction circuit being connected to said first summing means.

2. The monitor as claimed in claim 1 further comprising
    a generator of pressure vibrations having a frequency exceeding the frequency of the highest harmonic component of the blood pressure beat wave, said generator being connected through connection means to said transducer.

3. The monitor as claimed in claim 1 further comprising
    a generator of pressure vibrations having a frequency exceeding the frequency of the highest harmonic component of the blood pressure beat wave, said generator being connected through second summing means to said transducer;
    said generator of pressure vibrations being an oscillator;
    the correction circuit comprising a narrow band amplifier tuned to the frequency of the oscillator and connected to a first detector the output of which is connected to an evaluating circuit connected with a first integrator.

4. The monitor as claimed in claim 3 wherein
    the amplifier means comprises a first amplifier, and a second amplifier with electronic gain control;
    said second amplifier being connected through a high pass filter to a second detector and a second integrator, the output of which is connected to the gain control of the second amplifier.

5. The monitor as claimed in claim 3 wherein
    the plethysmographic gauge is a photoelectric reflection plethysmograph having a light sensor and a light source placed in an inner sheet of said pressure means.

6. The monitor as claimed in claim 3 wherein
    the plethysmographic gauge is a photoelectric reflection plethysmograph having a light sensor and a light source placed in an opposite rigid support in the neighbourhood of the measured artery.

7. The monitor as claimed in claim 1 wherein
    the amplifier means comprises a first amplifier, and a second amplifier with electronic gain control;
    said second amplifier being connected through a high pass filter to a second detector and a second integrator, the output of which is connected to the gain control of the second amplifier.

8. The monitor as claimed in claim 7 wherein
    the plethysmographic gauge is a photoelectric reflection plethysmograph having a light sensor and a light source placed in an inner sheet of said pressure means.

9. The monitor as claimed in claim 4 wherein
    the plethysmographic gauge is a photoelectric reflection plethysmograph having a light sensor and a light source placed in an opposite rigid support in the neighbourhood of the measured artery.

10. The monitor as claimed in claim 1 wherein
    the plethysmographic gauge is a photoelectric reflection plethysmograph having a light sensor and a light source placed in an inner sheet of said pressure means.

11. The monitor as claimed in claim 1 wherein
    the plethysmographic gauge is a photoelectric reflection plethysmograph having a light sensor and a light source placed in an opposite rigid support in the neighbourhood of the measured artery.

* * * * *